(12) United States Patent
Kaikkonen et al.

(10) Patent No.: US 10,117,962 B2
(45) Date of Patent: Nov. 6, 2018

(54) ANTIPATHOGENIC COMPOSITIONS

(71) Applicant: Ozics Oy, Tampere (FI)

(72) Inventors: Auvo Kaikkonen, Sliema (MT);
Juha-Pekka Nuutinen, Tampere (FI);
Andreas Posel, Swieqi (MT)

(73) Assignee: Servico Group Oy (FI)

( * ) Notice: Subject to any disclaimer, the term of this patent is extended or adjusted under 35 U.S.C. 154(b) by 550 days.

(21) Appl. No.: 14/390,053

(22) PCT Filed: Mar. 13, 2013

(86) PCT No.: PCT/IB2013/000910
§ 371 (c)(1),
(2) Date: Oct. 2, 2014

(87) PCT Pub. No.: WO2013/150377
PCT Pub. Date: Oct. 10, 2013

(65) Prior Publication Data
US 2016/0074555 A1    Mar. 17, 2016

Related U.S. Application Data

(60) Provisional application No. 61/619,458, filed on Apr. 3, 2012.

(51) Int. Cl.
*A61L 27/54* (2006.01)
*C08L 33/10* (2006.01)
*A61L 24/00* (2006.01)
*A61L 27/44* (2006.01)
*A61M 5/315* (2006.01)

(52) U.S. Cl.
CPC ....... *A61L 24/0015* (2013.01); *A61L 24/0089* (2013.01); *A61L 27/446* (2013.01); *A61L 27/54* (2013.01); *A61M 5/31596* (2013.01); *A61L 2300/404* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 4,775,646 A * | 10/1988 | Hench | ..................... | A61L 27/12 428/432 |
| 5,276,068 A * | 1/1994 | Waknine | ................... | C09J 4/00 433/222.1 |
| 5,444,104 A * | 8/1995 | Waknine | ................... | C09J 4/00 433/222.1 |
| 5,681,872 A * | 10/1997 | Erbe | ................... | A61B 17/866 106/35 |
| 5,756,145 A * | 5/1998 | Darouiche | .......... | A61F 2/30767 427/2.24 |
| 6,270,562 B1 * | 8/2001 | Jia | ........................ | A61K 6/0091 106/35 |
| 6,455,608 B1 * | 9/2002 | Jia | ........................ | A61K 6/0038 433/228.1 |
| 6,800,671 B1 * | 10/2004 | Montgomery | ........ | A61L 24/046 523/105 |
| 2007/0049656 A1 * | 3/2007 | Jia | ......................... | A61K 6/083 523/116 |
| 2016/0074555 A1 * | 3/2016 | Kaikkonen | ........... | A61L 27/446 604/82 |

OTHER PUBLICATIONS

Caprolactone 2-(methacryloyloxy)ethyl etster, Aldrich, 2017, pp. 1-3.*

* cited by examiner

*Primary Examiner* — Peter A Salamon
(74) *Attorney, Agent, or Firm* — Banner & Witcoff, Ltd.

(57) ABSTRACT

Compositions useful as bone fillers or dental composites are provided which may include a sterilizing agent.

11 Claims, No Drawings ated Mar. 13, 2013; which claims priority to U.S. Provisional Application No. 61/619,458, filed on Apr. 3, 2012 each of which are hereby incorporated by reference in their entireties.

ANTIPATHOGENIC COMPOSITIONS

RELATED APPLICATION DATA

This application is a National Stage Application under 35 U.S.C. 371 of co-pending PCT application PCT/IB2013/000910 designating the United States and filed Mar. 13, 2013; which claims priority to U.S. Provisional Application No. 61/619,458, filed on Apr. 3, 2012 each of which are hereby incorporated by reference in their entireties.

FIELD

The present invention relates to antipathogenic compositions, such as those useful as curable implants.

BACKGROUND

Growth of pathogenic agents within or on compositions to be placed within the body, such as for example in treating bone defects or conditions, is undesirable. Such compositions are often placed in containers or packages where they are then stored and remain until just prior to use. Such compositions may be subject to growth of pathogenic agents while in storage thereby rendering them unsuitable for placement within the body.

A composition where glutaraldehyde is used to bond to collagen is the subject matter of U.S. Pat. No. 4,814,423. A bone cement composition including hydrogen peroxide and a stabilizer is the subject matter of US 2010/0159027. A method of sterilizing viscous, multi-component compositions is the subject matter of US 2010/0226820 where monomers are passed through a filter and then combined with other sterile components. In addition, other sterilizations methods are known which include application of radiation and exposure to a vapor or gas such as ethylene oxide. However, application of radiation for purposes of sterilization can lead to unwanted polymerization of a bone cement composition. Also, vapors or gases used for purposes of sterilization may not be able to penetrate into a bone cement composition, especially, when the bone cement composition is already packaged. There is a need for sterile compositions used in the treatment of bone fractures, bone repair, bone augmentation and the like. There is a need for compositions used in the treatment of bone fractures, bone repair, bone augmentation and the like which are sterile within packaging. There is a further need for methods of sterilizing compositions used in the treatment of bone fractures, bone repair, bone augmentation and the like or otherwise rendering compositions used in the treatment of bone fractures, bone repair, bone augmentation and the like antipathogenic, sporicidal, antibacterial, antifungal, antiyeast and the like.

Accordingly, one object of the present disclosure is directed to compositions for use as curable implants that include an antipathogenic agent, such as a sporicidal agent or an antibacterial agent or an antifungal agent or an antiyeast agent. An additional object is directed to methods of making a composition for use as a curable implant includes an antipathogenic agent. A still further object is directed to compositions for use as a curable implant which are sterile within packaging. A still further object is directed to methods of lowering the risk of infection to patients into which a composition including an antipathogenic agent is placed. These and other objects, features, and advantages of the invention or certain embodiments of the invention will be apparent to those skilled in the art from the following disclosure and description of exemplary embodiments.

SUMMARY

Embodiments of the present disclosure are directed to compositions for use as curable implants. According to one aspect, the compositions are curable to produce a cured implant having load bearing properties sufficient for use as implants in the treatment of bone fractures, bone repair, bone augmentation, and as dental composites. According to one aspect, the compositions include an antipathogenic agent and are curable to produce a cured implant having load bearing properties sufficient for use as implants in the treatment of bone fractures, bone repair, bone augmentation, and as dental composites. Certain compositions of the present disclosure may be referred to as dental composites, bone cements, bone fillers, bone void fillers, bone implants, bone augmentation materials, bone reinforcing composites and the like. Compositions described herein include one component systems or multi-component systems, such as a two component system, where components are mixed together immediately prior to use or substantially immediately prior to use. Compositions described herein include formulations in uncured or cured form. According to one aspect, compositions of the present disclosure include an effective sterilizing amount of one or more sterilizing agents or antipathogenic agents.

One component systems are generally understood to include flowable mixtures or putties contained within a package that are removed from the package and then cured by a curing mechanism. One component systems can begin curing after removal from packaging and prior to administering to an individual. Curing can also occur within the individual. One component compositions or systems are generally understood to include flowable mixtures or putties contained within a package that are removed from the package, applied to a desired site within the body, such as a bone or a tooth, and then cured by a curing mechanism. Such one component compositions or systems may have a viscosity between a liquid and a putty. According to one aspect, such one component compositions of the present disclosure include an effective sterilizing amount of one or more sterilizing agents or antipathogenic agents.

Multi-component compositions or systems are generally understood to include two or more components that are maintained in separate packages, compartments, vessels, containers and the like and are combined or mixed prior to use, such as by a surgeon or other medical health professional, intending to treat an individual with the composition or otherwise administer the composition to an individual in need thereof. Multicomponent systems can begin curing after mixing and prior to administering to an individual. Curing can also occur within the individual. Components of the multi-component composition or system may be in dry powder form or liquid form and are combined to produce a composition that is then cured by a curing mechanism. Components of the multi-component composition or system may be in dry powder form or liquid form and are combined to produce a composition that is then applied to a desired site within the body. Curing by a curing mechanism can begin prior to administration to an individual and while within an individual. The composition resulting from combination of the multi-components may have a viscosity between a liquid and a putty. According to one aspect, such multi-component compositions of the present disclosure include an effective sterilizing amount of one or more sterilizing agents or antipathogenic agents.

The term "flowable" as used herein applies to compositions whose consistencies range from those which can be described as shape-sustaining but readily deformable, e.g., those which behave like putty, to those which are gel like, to those which are runny or fluid. In an exemplary embodiment of the invention, the flowable composition is capable of passing through a syringe or cannula.

According to certain aspects, compositions of the present disclosure include one or more antipathogenic agents. The antipathogenic agent can be within a one-component composition or system or within one or more or all components of a multi-component composition or system such that the mixture resulting from the multi-components includes one or more antipathogenic agents. According to one aspect, compositions of the present disclosure are rendered antipathogenic by the inclusion therein of one or more antipathogenic agents. According to one aspect, the antipathogenic agent is present in the components of the composition or in the composition in an effective antipathogenic amount or an effective sterilizing amount. The components of the composition or the composition is then placed into packaging where it remains antipathogenic or sterile. The antipathogenic components of the composition or the composition can then be removed from the packaging and used. According to certain aspects, the components of the composition or the compositions described herein are antipathogenic, such as sporidical, antimicrobial, antibacterial, antifungal, antiyeast and the like.

According to certain aspects, the one or more antipathogenic agents are physically mixed or otherwise physically homogeneously distributed within a one-component composition or within one or more or all components of a multi-component composition. The presence of the one or more antipathogenic agents in the components of the composition or the composition renders the components of the composition or the composition antipathogenic or sterile. According to this aspect, if the component of the composition or the composition was non-sterile before addition of the antipathogenic agent, the antipathogenic agent would render the component of the composition or the composition sterile and would remain sterile for a useful period of time. Accordingly, the one-component composition or the one or more or all components of a multi-component composition may be in a non-sterile or sterile condition prior to the addition of the antipathogenic agent. The one-component composition or the one or more or all components of a multi-component composition may be subjected to methods and agents known to those of skill in the art that are useful in sterilizing compositions disclosed herein.

In certain embodiments, the ability of pathogenic microorganisms, i.e. pathogens such as microbes and/or bacteria and/or fungi and/or yeast to adhere, proliferate, be virulent and/or colonize within or to the one-component composition or the one or more or all components of a multi-component composition or the resulting mixture of the one or more or all components of a multi-component composition is prevented, decreased, inhibited and/or reduced. According to one aspect, the one-component composition or the one or more or all components of a multi-component composition or the resulting mixture of the one or more or all components of a multi-component composition is rendered sterile by the antipathogenic agent and its presence within and throughout the one-component composition or the one or more or all components of a multi-component composition or the resulting mixture of the one or more or all components of a multi-component composition. It is to be understood that pathogenic microorganisms include microbes, bacteria, fungus and yeast specific examples of which will be readily apparent to those of skill in the art based on the present disclosure and available references. According to one aspect, the antipathogenic agent prevents, decreases, inhibits and/or reduces the ability of pathogenic microorganisms, i.e. pathogens such as microbes and/or bacteria and/or fungi and/or yeast to adhere, proliferate, be virulent and/or colonize within or to the one-component composition or the one or more or all components of a multi-component composition or the resulting mixture of the one or more or all components of a multi-component composition thereby reducing the risk of infection or illness due to the presence of pathogens when the one component composition or the resulting mixture of the one or more or all components of a multi-component composition is placed in the body.

Embodiments of the present disclosure are directed to methods of reducing the risk of pathogenic infection, such as microbial or bacterial or fungal or yeast infection from the insertion or implantation of compositions described herein into an individual. According to the methods, the presence of live microbes or bacteria or fungus or yeast is reduced or eliminated in compositions including one or more antipathogenic agents described herein, for example when compared to a composition lacking antipathogenic agents described herein, thereby reducing the risk of infection or illness due to the presence of live microbes or bacteria or fungus or yeast. The mechanism for reducing the amount of live microbes or bacteria or fungus or yeast can include cell death, reduced cell adhesion, reduced cell proliferation, or reduced cell differentiation. According to one aspect, the compositions of the present disclosure are rendered sterile, i.e. no or substantially no live microbes or bacteria or fungus or yeast, by the presence of one or more antipathogenic agents within the composition and accordingly, the risk of pathogenic infection resulting from insertion or implantation of the composition is reduced.

DETAILED DESCRIPTION

The principles of the present invention may be applied with particular advantage to provide compositions including an antipathogenic agent or sterilizing agent to be inserted into the body. The antipathogenic agent sterilizes and/or disinfects the composition or component into which it is mixed. The term "sterile" as used herein means that a composition is free from viable or live microorganisms. The term "disinfect" as used herein means that a composition is free of or substantially free of viable or live microorganisms. An antipathogenic agent may be capable of sterilizing or disinfecting a composition described herein. Methods for determining sterility are provided in ISO 11137-2 hereby incorporated by reference in its entirety. According to certain aspects, a composition or one or more or all components of a multi-component composition include one or more antipathogenic agents which are included in or otherwise stored in packages, compartments, vessels, containers and the like.

According to one aspect, a dental composite composition, dental reconstruction material or dental filling material includes one or more antipathogenic agents or sterilizing agents. According to one aspect, a bone cement composition includes one or more antipathogenic agents or sterilizing agents. According to one aspect, a bone filler composition includes one or more antipathogenic agents or sterilizing agents. According to one aspect, a bone void filler composition includes one or more antipathogenic agents or sterilizing agents. According to one aspect, a bone implant composition includes one or more antipathogenic agents or sterilizing agents. According to one aspect, a bone augmentation material includes one or more antipathogenic agents or sterilizing agents. According to one aspect, a bone reinforcing composite includes one or more antipathogenic agents or sterilizing agents. According to one aspect, the composite or compositions are curable into a solid structure having load bearing properties sufficient to be useful as a dental prosthesis or implant, dental reconstruction material, dental filling material, dental cement material, bone cement composition, bone filler composition, bone void filler composition, bone implant composition, bone cement composition, bone augmentation material or bone implant material.

According to one aspect, the composition or resulting mixture of one or more or all components of a multi-component composition are sterile when stored, such as when present in packages, compartments, vessels, containers and the like, and upon dispensing for use in the body. According to certain aspects, the one or more antipathogenic agents promote or otherwise render the composition or resulting mixture of one or more components of a multi-component composition sterile without adversely altering the characteristics of the composition or resulting mixture of one or more components of a multi-component composition to function, for example, as dental prosthesis or implant, a dental reconstruction material, a dental filling material, a dental cement material, a dental composite, a bone cement, a bone filler, a bone void filler, a bone implant, a bone augmentation material, a bone reinforcing composite and the like.

According to certain aspects, the packages, compartments, vessels, containers and the like maintain the composition in a sterile condition. Such packages, compartments, vessels, containers and the like may be sealed in a manner to preserve sterility inside the packages, compartments, vessels, containers and the like and prevent contamination from non-sterile conditions outside of the packages, compartments, vessels, containers and the like. Such packages, compartments, vessels, containers and the like may be rendered sterile using methods known to those of skill in the art prior to introduction of the compositions of the present disclosure. Such packages, compartments, vessels, containers and the like may be rendered sterile by an antipathogenic agent or sterilizing agent contained within a particular composition or formulation introduced into such packages, compartments, vessels, containers and the like. Once compositions are introduced into such packages, compartments, vessels, containers and the like, such packages, compartments, vessels, containers and the like may be securely or hermetically sealed according to methods known to those of skill in the art, thereby preserving the sterile nature of the composition or formulation.

The present disclosure contemplates delivery devices to allow for the storage and/or dispensing and/or premixing of the compositions described herein. Delivery devices within the scope of the present disclosure include single chamber or multi chamber syringe devices, such as dual chamber syringe devices known to those of skill in the art. Such dual chamber delivery devices may include a mixing device such as a static mixer to accomplish mixing or blending of a two component system prior to application of the blended composition to an individual. Such dual chambered delivery devices are commercially available from Medmix AG.

Compositions within the scope of the present disclosure include viscous sterile liquid or paste compositions that are blended to include one or more antipathogenic agents or sterilizing agents in an amount to render the composition antipathogenic or sterile. According to one aspect, compositions within the scope of the present disclosure include viscous sterile liquid or paste compositions that are homogeneously blended to include one or more antipathogenic agents or sterilizing agents in an amount to render the composition antipathogenic or sterile. The compositions may have a viscosity between about 40,000 centipoise to about 100,000,000 centipoise as measured by a Brooksfield viscometer. Methods of measuring viscosity are known to those of skill in the art. Shear viscosity can also be measured. Methods of measuring shear viscosity are known to those of skill in the art and include use of an Anton-Paar Rotational rheometer MCR-301, plate-plate geometry using shear rates from 1 to 100 l/s. Exemplary shear viscosities are between about 5 Pa*S to about 10,000 Pa*s.

Exemplary compositions described herein include one or more curable compounds and one or more fillers. Curable compounds include those commonly known as cements and those commonly known as polymerizable compounds. Curable cements include those known in the art and commercially available for use as dental composites or cements and bone composites or cements which do not cure by polymerization. Polymerizable compounds include polymerizable monomers or polymers or resin components. Fillers include glass fillers. Exemplary compositions described herein include one or more curable compounds, such as cements or polymerizable compounds, one or more fillers and one or more antipathogenic agents or sterilizing agents. Depending upon the curing mechanism, exemplary compositions may include one or more initiators, accelerators and/or inhibitors know to those of skill in the art to induce and control polymerization or other ingredients known to those of skill in the art useful in a dental prosthesis or implant, a dental reconstruction material, a dental filling material, a dental cement material, a bone cement composition, a bone filler composition, a bone void filler composition, a bone implant composition, a bone cement composition, a bone reinforcing composite, a bone augmentation material or a bone implant material.

Exemplary curable cements include calcium phosphate cements, calcium sulfate cements and the like. Calcium phosphate cement compositions are commercially available and include HydroSet, BoneSource, α-BSM, Biobon, Calcibon, ChronOS inject and Norian SRS. Calcium phosphate bone cements generally include one or more of amorphous calcium phosphate, dicalcium phosphate dehydrate, dicalcium phosphate anhydrous, α-tricalcium phosphate, dicalcium phosphate, tetracalcium phosphate, monocalcium phosphate monohydrate, trisodium citrate and calcium carbonate. A suitable fluid for the calcium phosphate cement includes a sodium phosphate solution which may include sodium phosphate, water and polyvinylpyrrolidone. Calcium sulfate cements are commercially available and include MIIG 115 and MIIG X3. Calcium sulfate bone cements includes one or more of calcium sulfate hemihydrate, α-calcium sulfate hemihydrate, and β-calcium sulfate hemihydrate.

Calcium phosphate cements or calcium sulfate cements may be made by blending dry powder ingredients with a liquid ingredient by hand using a spatula or by a conventional blending apparatus. The blended cements may then be transferred, for example, to a suitable syringe apparatus for application to a bone site within an individual.

Exemplary compositions of the present disclosure include a liquid polymerizable compound component and a powder filler component, such as a powder glass component. Exemplary compositions of the present disclosure include a liquid polymerizable compound component, a powder filler component, such as a powder glass component, and an antipathogenic agent or sterilizing agent. According to certain aspects, exemplary powder to liquid ratios for exemplary compositions can be obtained using an amount of powder within a range of between about 60 wt % to about 75 wt % of the powder and liquid mixture. That is, exemplary powder to liquid ratios are within the range of about 0.60 to about 0.75.

Embodiments of the present disclosure include polymerized or cured compositions of one or more curable compounds, such as polymerizable compounds, such as polymerizable monomers or polymers or resin components, one or more fillers, such as a glass filler, and one or more antipathogenic agents or sterilizing agents. Such polymerized or cured compositions may be characterized by a cured polymer network or phase or a cured cement phase with a dispersed filler phase and with a dispersed antipathogenic agent or sterilizing agent. Depending upon the curing mechanism, exemplary polymerized or cured compositions may include initiators known to those of skill in the art that induce polymerization or other ingredients known to those of skill in the art useful in a dental prosthesis or implant, a dental reconstruction material, a dental filling material, a dental cement material, bone cements, bone fillers, bone void fillers, bone augmentation materials, bone implants, or bone reinforcing composites and the like, such as calcium phosphates.

According to one aspect, relatively low viscosity, syringable pastes have application for introduction into bony defects, or tooth defects or for repairing fractures, and securing implants. The compositions of the present disclosure may have a viscosity sufficient to fill voids in bone or teeth, crevices in bone or teeth, breaks in bone or teeth, and the like, or otherwise be fashioned or sculpted to fill fracture sites. A viscous liquid formulation can be syringed into a bone or tooth void, crevice, break, fracture or the like, or a putty formulation can be fashioned, manipulated, sculpted and cured in place.

According to certain aspects, the curable compounds and fillers may be initially and individually sterilized but need not be. The curable compounds and fillers may be blended together to form one or more viscous pastes. The curable compounds and fillers may be blended together with one or more antipathogenic agents or sterilizing agents to form one or more viscous pastes in sterile condition. The paste is packaged within a delivery vessel which may be a sterile delivery vessel. The delivery vessel may include one or more chambers or cartridges to house the formulation or composition or components of the formulation or composition. In multi-component systems, the components are dispensed from their respective cartridges or chambers and blended together within the delivery vessel or within a static mixing cannula attached to the delivery vessel to form at least one viscous, homogeneous blend or composition immediately prior to or upon dispensing.

The one or more curable compounds form a three dimensional cured matrix within which is dispersed a filler and an antipathogenic agent and other ingredients known to those of skill in the art of a dental prosthesis or implant, a dental reconstruction material, a dental filling material, a dental cement material, bone cements, bone fillers, bone void fillers, bone augmentation materials, bone implants, or bone reinforcing composites and the like.

The polymerizable compounds may be monomers or dimers or trimers and include ethylenically unsaturated monomers, dimers or trimers. The polymerizable compounds may include crosslinking functional groups or a crosslinking compound may be included to provide crosslinking. The one or more polymerizable compounds form a three dimensional cured matrix within which is dispersed a filler and an antipathogenic agent and other ingredients known to those of skill in the art of a dental prosthesis or implant, a dental reconstruction material, a dental filling material, a dental cement material, bone cements, bone fillers, bone void fillers, bone augmentation materials, bone implants, or bone reinforcing composites and the like. Examples of ethylenically unsaturated monomers, dimers or trimers include polymerizable compounds having one or more acrylate moieties or one or more acrylate functional groups. Polymerizable compounds include mono- and dimethacrylate compounds. The acrylate compounds, such as acrylate monomers, may include esters of acrylic acid or methacrylic acid. The acrylate compound or monomer may include one or more acrylate or methacrylate moieties per acrylate molecule.

The term "monomers", as used herein, can also represent dimers, trimers, resins, resin components, or any other polymerizable component. Representative polymerizable compounds are commercially available from Esstech, Polysciences or other suitable commercial vendors known to those of skill in the art. Examples of the monomers include, but are not limited to, acrylates, methacrylates, bisphenol A glycidyl dimethacrylate (Bis-GMA), hydroxyethylmethacrylate (HEMA), 2-hydroxyethyl methacrylate phosphate, pyromellitic dimethacrylate, bis(methacryloxyethyl) phosphate, 4-methacyloxyethyl trimellitic anhydride, poly(propyleneglycol) dimethacrylate, poly(propyleneglycol) 425 dimethacrylate, poly(propyleneglycol) monomethacrylate, poly(propyleneglycol) 300 monomethacrylate, tri(ethylene glycol) dimethacrylate (TEGDMA), urethane dimethacrylate (UDMA), modified urethane dimethacrylate (FIT 852 resin, Esstech), 1-10 decanediol dimethacrylate (D-DMA), bisphenol-A-diglycidyl methacrylate (bis GMA), triethyleneglycol dimethacrylate (TEGDMA), bisphenol-A-ethyl methacrylate (Bis-EMA), pentaerythritol tetraacrylate, 1-(acryloyloxy)-3-(methacryloyloxy)-2-propanol, 1,10-decanediol dimethacrylate, 1, 3-butanediol dimethacrylate, 1,3-glyceryl dimethacrylate, 1,4-butanediol diacrylate, 1,4-butanediol dimethacrylate, 1,4-diacryloylpiperazine, 1,4-phenylene diacrylate, 1,5-pentanediol dimethacrylate, 1,6-hexanediol diacrylate, 1,6-hexanediol dimethacrylate, 1,9-nonanediol dimethacrylate, 2,2-Bis(4-methacryloxyphenyl) propane, 2,2-Bis[4-(2acryloxyethoxy)phenyl]propane, 2,2-Bis[4-(2-hydroxy-3-methacryloxypropoxy)phenyl]propane, 2,2-dimethylpropanediol dimethacrylate, 2-hydroxypropyl acrylate, 4-hydroxybutyl acrylate, barium methacrylate, Bis (2-methacryloxyethyl) N,N'-1,9-nonylene biscarbamate, Bis (2-methacryloxyethyl) phosphate, Bisphenol A-bis(2-hydroxypropyl) acrylate, Copper (II) methacrylate, diethylene glycol diacrylate, diethylene glycol dimethacrylate, ethylene glycol diacrylate, ethylene glycol dimethacrylate, fluorescein dimethacrylate, lead acrylate, magnesium acrylate, N, N' ethylene bisacrylamide, N,N'-hexamethylenebisacrylamide, N,N'-methylenebisacrylamide, N,N'-cystaminebisacrylamide, N,N-diallylacrylamide, N-hydroxyethyl acrylamide, tetraethylene glycol dimethacrylate, trans-1,4-cycolhexanediol dimethacrylate, tricyclodecane dimethanol diacrylate, triethylene glycol diacrylate, triethylene glycol dimethacrylate, zinc (di)methacrylate and the like In preferred embodiments, the monomers within the paste composition are activated or otherwise capable of polymerizing prior to sterilization. Unsaturated compounds, such as methacrylates, can be polymerized by free radical chain polymerization. Free radicals are produced by a chemical initiator and initialize polymerization by breaking the double bond of the acrylate group creating reactive species with an active center. These reactive species join together and the active center moves to the end of the polymer chain when a new monomer radical joins it. Certain initiator free radicals that initiate polymerization are independent species which have an unpaired electron and short half-lives. Energy input as heat or light or the use of an activator or accelerator can enhance initiator free radical production. Inhibitor compounds can scavenge free radicals to control the population of free radicals in a composition.

In certain embodiments, the monomers may be activated, for example, by the addition of benzoyl peroxide (BPO, Polysciences) or other free radical formers and tertiary amines, or other reducing agents, such as but not limited to DHEPT, DMAPE, DMEPT, ascorbic acid, that may provide an electron withdrawing group that initiates free radical polymerization. Certain "starter systems" are known to those of skill in the art and include BPO and an accelerator, dimethyl-p-toluidene (DMPT, Aldrich). Certain inhibitor compounds are known in the art such as antioxidants for example butylated hydroxytoluene (BHT, Fluka).

According to certain aspects for a two component system, BPO is mixed into a first component and DMPT is mixed into a second component. When the first component and the second component are mixed together, free radicals are formed which lead to polymerization of the mixture. Either the first component or the second component or both may include a stabilizer or scavenger compound which act to bind to free radicals which may be present in each component thereby inhibiting or impeding pre-mature polymerization or auto-polymerization.

The pastes of the present invention may further comprise, but are not limited to, polymerization inhibitors, polymerization activators, polymerization initiators, radiopacifiers, reinforcing components (i.e., fibers, particles, micro spheres, flakes, etc.), bioactive fillers, neutralizing resins, diluting resins, antibiotic agents, coloring agents, plasticizers, coupling agents, free radical generators, radiographic contrast agents, and antibiotics.

Polymerization inhibitors may be added to the composition to minimize polymerization during storage. Examples of polymerization inhibitors include free radical scavengers. Exemplary free radical scavengers include hydroquinone, and various functional equivalents such as butylhydroxytoluene (BHT), UV-9, methyl ether hydroquinone (MEHQ), 4-benzyloxy phenol and 3,5-diisopropyl phenol and the like.

Polymerization activators are typically amines and are used to promote free radical generation from organic peroxide initiators in addition polymerizations. The free radicals are generated at temperatures around room temperature or below by chemical reduction of the peroxide. Examples of such activators are, N,N-dimethyl-p-toluidine (DMEPT), dihydroxyethyl-p-toluidine (DHEPT), N,N-dimethyl-meta-toluidine, N,N-dimethyl-ortho-toluidine, N-ethyl-N-hydroxyethyl-meta-toluidine, magnesium salt of N-tolylglycine glycidylmethacrylate (NTG-GMA ($Mg^{+2}$)), or sodium salt of N-tolylglycine glycidylmethacrylate (NTG-GMA ($Na^+$)). Polymerization activators are commercially available from Esstech, Inc.

Color agents may be added to the composition to impart color and may include dyes, paint pigments, or reduced metal particles.

Plasticizers may be added to the composition to facilitate processing and increase the flexibility of the final product. Examples of plasticizers include TEGDMA, HEMA and phthalates such as diethyl phthalate, benzylbutyl phthalate, dibutyl phthalate, and dibenzyl phthalate.

Coupling agents are used to link the filler within the composition to the polymer matrix. Typical coupling agents include silanes such as γ-methyacryloxypropyltrimethoxysilane or other cationic coupling agents.

Free radical generators are substances within the composition that decompose to form free radicals that begin the process of polymerization. Examples of free radical generators include benzoyl peroxide, tert-butyl peroxide, and diethyl peroxide.

Radiographic or diagnostic contrast agents may be added to the composition to enable the composition to be discerned upon X-ray or other diagnostic means. Examples of such agents include barium boroaluminosilicate glasses and glass-ceramics, barium sulfate ($BaSO_4$), zirconium dioxide ($ZrO_2$), chromium oxide (CrO), titanium oxide, Ta, Gd or other heavy metal particulate, or bismuthic compounds such as $Bi_2O_3$ and $Bi(OH)_3$.

In addition to the monomer, the viscous paste or pastes further comprise one or more fillers. These fillers may possess a variety of morphologies such as, but not limited to, needles, particulates, flakes, cylinders, short fibers, long fibers, whiskers, or spherical particles. In preferred embodiments, the filler is comprised of particles with an average particle size ranging from about less than 1.0 μm up to several millimeters (mm). Average particle sizes include those in the nanometer range, such as between about 1 nm to about 1000 nanometers, about 10 nm to about 500 nanometers, about 100 nm to about 300 nanometers and sizes and ranges in between. Preferably, the average particle size distribution ranges from 5 to 20 μm. The filler may be comprised of an inorganic or organic material. In certain embodiments, the filler is comprised of an inorganic material, such as a glass. In certain embodiments, the filler is a silica based filler, such as an unreactive silica based filler. In certain embodiments, the filler has a silane coupling agent including a functional group that can bind to the filler surface, such as a glass filler, and a functional group, such as a methacrylate group, that can polymerize with the polymerizable compound or compound. Such a filler provides a chemical bond between the polymer phase and the filler phase in the cured material which improves the strength of the composite. Filler glasses are known to those of skill in the art and are commercially available. Filler glasses include silanated and nonsilanated filler glasses. Useful filler glasses include those identified in the Table below.

| Type | | Silanated? | Abreviation | Name | Size (μm) (d50) | Supplier | Composition (largest first) |
|---|---|---|---|---|---|---|---|
| Unreactive | PARTICLE | NO | esschem 0.7 μm | EEG-102-07-S | 0.7 | Esschem | BaO, $SiO_2$, $B_2O_3$, $Al_2O_3$ |
| | | NO | Schott GM K6 | GM27884 | 2.67 | Schott | $SiO_2$, BaO, $B_2O_3$, $Al_2O_3$ |
| | | NO | Schott GM K5 | GM27884 | 5.26 | Schott | |
| | | NO | G018 090 K6 | G018-090 | 3.7 | Schott | $SiO_2$, SrO, $Al_2O_3$, F, ZnO, $P_2O_5$, $Na_2O$ |
| | | NO | G018 090 K4 | G018-090 | 7.08 | Schott | |
| | FIBRE | NO | Kevlar | Chopped Kevlar Fibre | | | |
| | | YES | GL 0271F | silane coated borosilicate glass fibre | 15 × 300 | MO-SCI | |
| | PARTICLE | YES | Fuji | Fuji IILC | ~5 | Fuji | Sr, Si, Al, F |
| | | YES | G018 117 sil | silanated G018-117 | 2 | Schott | |
| | | YES | GM27884 sil | silanated GM27884 | 2 | Schott | |
| | | YES | IF-2019 | IF-2019 Barium Boro alumino silicate glass | | Scl-pharm | |
| | | YES | IF-2025 | IF-2025 Boro alumino silicate glass | | Scl-pharm | |
| | | YES | GL 0179P | silane coated borosilicate frit | 1 to 10 | MO-SCI | |
| Reactive | | NO | P303S | porous P303 S | 2.43 | Plasma-Biotal | $Ca_3(PO_4)_2$ |
| | | NO | nanoXIM | nanoXIM bTCP | 5 | Fluidnova | Ca3(PO4)2 |
| | | NO | P292S | P292 S dense | 16.91 | Plasma-Biotal | $Ca_3(PO_4)_2$ (with UDMA and TEG) |
| | | NO | 30μ P292S | 30micron P292S bTCP | 30 | Plasma-Biotal | Ca3(PO4)2 |
| | | NO | SSB | Himed SSB210907 - solid state sintering process | 12.03 | Himed | beta-Ca3(PO4)2 |
| | | NO | SWB | Himed SWB101109 - wet precipitate sintering process | 11.24 | Himed | Ca3(PO4)2 |
| | | NO | Himed | himed MCPM | <30 | Himed | Ca(H2PO4)2—H2O (with UDMA and TEG) |

Examples of suitable fillers include, but are not limited to, barium glass, barium-boroaluminosilicate glass, silica, hydroxyapatite, calcium phosphates, tricalcium phosphate, 45S5 glass, bioactive glass, ceramics, glass-ceramics, bioactive synthetic combeite glass-ceramic or combinations thereof. The filler or fillers are generally pre-dried prior to blending with other fillers. In certain embodiments, one or more fillers may be coated with silane. One exemplary filler is a silane coated glass fiber. Additional fillers may include glass ionomer composites, light curable PLAs, polyanhydrides or other curable polymers, polyurethanes, cyanoacrylates, calcium-phosphates, calcium-sulphates or compositions thereof. Additional fillers may include TCP (tricalciumphosphate), nano-TCP, glass beads, diameter of which is preferably 0.1-1.0 mm, magnesium spheres or other metallic spheres or powder, glass fibers, silicone carbide, carbon fibers, polymer spheres such as PMMA beads, polymer fibers, radiopaque fillers, such as BaSO4, titanium oxide or compositions thereof.

According to certain aspects, the filler and polymerizable compound are combined to form one or more paste compositions. Equipment used to blend the paste or pastes is commercially available. Mixing equipment, such as the spatulas, blades etc., are preferably pre-sterilized using steam or autoclave sterilization or other methods well known to those of skill in the art such as dry heat sterilization or cold sterilization such as by using a sterilizing compound.

The paste is preferably contained within a primary packaging which may be sterilized prior to the filling of the paste or pastes. In certain embodiments, the primary packaging is sterilized via gamma sterilization, x-ray radiation or e-beam radiation.

Antipathogenic agents within the scope of the present disclosure include those commonly known in the art and described in Sagripanti et al., Applied and Environmental Microbiology, (1996), pp. 545-551 and Russel, Clinical Microbiology Reviews (1990) p. 99-119 each of which are hereby incorporated by reference in their entireties. Exemplary antipathogenic agents include organic acids, benzoic acid, scorbic acid, organic esters, parabens, methyl, ethyl, propyl and butyl esters of para-(4)-hydroxy benzoic acid, quaternary ammonium compounds, biguanides, chlorhexidine, chlorhexidine diacetate, chlorhexidine gluconate, organomercurial compounds, phenylmercuric nitrate, phenyl mercuric acetate, phenyl mercuric acid, merthiolate, alcohols, ethanol, methanol, propan-1-ol, propan-2-ol, phenyl ethanol, aldehyde compounds, glutaraldehyde, formaldehyde, glyoxal, malonaldehyde, succinaldehyde, adipaldehyde, halogen compounds, iodine, iodine compounds, iodophors, chlorine, chlorine compounds, chlorine releasing compounds, calcium hypochlorite, sodium dichloroisocyanusate, hypochlorous acid, mercuric chloride, benzalkonium chloride, cetylpyridinium chloride, hydrogen peroxide, peroxy acids, peracetic acid, peroxygens, propiolactone, β-propiolactone, peracetic acid, cupric ascrobate, sodium hypochlorite, sodium thioglycolate, phenol, cresol, chlorocresol and the like.

According to one aspect, one or more antipathogenic agents can be included in the compositions described herein. The one or more antipathogenic agents are included in a sterilizing effective amount.

The one or more antipathogenic agents are included in a disinfecting effective amount. According to one aspect, the antipathogenic agent may be present in the composition in an amount between about 0.1% to about 5.0% based on the weight of the composition. An exemplary antipathogenic or sterilizing agent is glutaraldehyde or glutar(di)aldehyde. According to certain aspects, the antipathogenic agent may be present in the composition in an amount between about 0.5% to about 4.0% by weight of the composition, about 1.0% to about 3.0% by weight of the composition, about 1.5% to about 3.5% by weight of the composition, about 1.5% to about 2.5% by weight of the composition, about 1.75% to about 2.25% by weight of the composition, about 1.8% to about 2.1% by weight of the composition, about 1.9% to about 2.0% by weight of the composition, about 2% by weight of the composition by weight of the composition, about 1.5% to about 3.0% by weight of the composition, about 1.75% to about 2.75% by weight of the composition, about 2.0% to about 3.0% by weight of the composition, about 1.75% to about 3.0% by weight of the composition, about 2.0% to about 2.5% by weight of the composition, about 0.5% by weight of the composition or less, about 0.75% by weight of the composition or less, about 1.0% by weight of the composition or less, about 1.25% by weight of the composition or less, about 1.5% by weight of the composition or less, about 1.75% by weight of the composition or less, about 2.0% by weight of the composition or less, about 2.25% by weight of the composition or less, about 2.5% by weight of the composition or less, about 2.75% by weight of the composition or less or about 3.0% by weight of the composition or less. One of skill in the art will recognize based on the present disclosure that different sterilizing agents may be present in different sterilizing effective amounts based on the strength or ability of a sterilizing agent to deactivate or kill pathogens. One of skill in the art will recognize based on the present disclosure that different antipathogenic agents may be present in different sterilizing effective amounts or different disinfecting effective amounts based on the strength or ability of an antipathogenic agent to deactivate or kill pathogens.

According to one aspect, the pH of the component or composition of the present disclosure is between about 3.0 to about 9.0, between about 4.0 to about 8.0, between about 5.0 to about 8.0, between about 6.0 to about 8.0, between about 7.0 to about 8.0 or about 7.4.

The compositions of the present invention can also include bioactive molecules effective to achieve a desired result. Suitable bioactive molecules include, but are not limited to, growth factors, anti-inflammatory agents, wound healing agents, anti-scarring agents, antimicrobial agents (for example, silver), cell-adhesion peptides including Arg-Gly-Asp (RGD) containing peptides, nucleic acids, nucleic acid analogues, proteins, peptides, amino acids, and the like, or combinations thereof.

Pharmacologically active agents such as, for example, VEGF (vascular endothelial cell growth factor), FGF (the fibroblast growth factor family of proteins), TGFβ (transforming growth factor B), hepatocyte growth factor (HGF), platelet factor 4 (PF4), PDGF (platelet derived growth factor), EGF (epidermal growth factor), NGF (nerve growth factor), BMP (bone morphogenetic protein family), coagulation factors such as one of the vitamin K-dependent coagulant factors, such as Factor II/IIa, Factor VII/VIIa, Factor IX/IXa or Factor X/Xa. Factor V/Va, VIII/VIIIa, Factor XI/XIa, Factor XII/XIIa, Factor XIII/XIIIa, and mixtures thereof may also be used. Antibiotics, antifungal agents, hormones, enzymes, enzyme inhibitors, and mixtures thereof can also be incorporated in the compositions of the instant invention and subsequently delivered to the wound site.

Exemplary compositions within the scope of the present disclosure include one or more polymerizable compounds, one or more fillers, and one or more initiators, activators or inhibitors. According to a certain aspect, the one or more polymerizable compounds includes one or more or all of poly(propylene glycol) dimethacrylate, urethane dimethacrylate and hydroxyethylmethacrylate. According to a certain aspect, the one or more polymerizable compounds includes as a weight percent of the monomer component, about 40% to about 60% poly(propylene glycol) dimethacrylate, about 35% to about 55% urethane dimethacrylate and about 1% to about 10% hydroxyethylmethacrylate. According to a certain aspect, the one or more polymerizable compounds includes as a weight percent of the monomer component, about 50% poly(propylene glycol) dimethacrylate, about 45% urethane dimethacrylate and about 5% hydroxyethylmethacrylate.

According to one aspect, the one or more polymerizable compounds includes one or more or all of bis-phenol A glycidyl dimethacrylate (BisGMA), ethoxylated Bis-phenol A dimethacrylate (BisEMA) and triethylene glycol dimethacrylate (TEGDMA). According to one aspect, the BisGMA and BisEMA are present in a 1 to 1 ratio. According to a certain aspect, the one or more polymerizable compounds includes as a weight percent of the composition, about 10% to about 25% combined BisGMA and BisEMA, and 5% to about 15% TEGDMA. According to a certain aspect, the one or more polymerizable compounds includes as a weight percent of the composition, about 11% to about 23% combined BisGMA and BisEMA, and 7% to about 13% TEGDMA.

According to a certain aspect, the one or more initiators includes benzoyl peroxide. According to a certain aspect, the one or more initiators includes as a weight percent of the monomer component, about 0.1% to about 1.0% benzoyl peroxide. According to a certain aspect, the one or more initiators includes as a weight percent of the monomer component, about 0.5% benzoyl peroxide. According to a certain aspect, the one or more initiators includes as a weight percent of the composition, about 0.1% to about 4.0% benzoyl peroxide, or about 1.0% to about 4.0% benzoyl peroxide.

According to a certain aspect, the one or more activators includes N,N-dimethyl-p-toluidine. According to a certain aspect, the one or more activators includes as a weight percent of the monomer component about 0.1% to about 1.0% N,N-dimethyl-p-toluidine. According to a certain aspect, the one or more activators includes as a weight percent of the monomer component about 0.5% N,N-dimethyl-p-toluidine. According to a certain aspect, the one or more activators includes as a weight percent of the composition about 0.1% to about 5.0% N,N-dimethyl-p-toluidine, or about 2.0% to about 5.0% N,N-dimethyl-p-toluidine.

According to a certain aspect, the one or more inhibitors includes butylated hydroxytoluene (BHT), butylated hydroxyanisole (BHA) and vitamin-E. According to a certain aspect, the one or more inhibitors includes as a weight percent of the monomer component, about 60 ppm to about 80 ppm inhibitor, such as butylated hydroxytoluene. According to a certain aspect, the one or more inhibitors includes as a weight percent of the monomer component, about 70 ppm inhibitor, such as butylated hydroxytoluene. According to a certain aspect, the one or more inhibitors includes as a weight percent of the composition, about 0.1% to about 0.5% inhibitor or about 0.2% to about 0.5% inhibitor, such as butylated hydroxytoluene.

According to a certain aspect, the one or more fillers includes glass fibers. According to a certain aspect, the one or more fillers includes glass fibers as a weight percent of the filler of about 15% to about 35% glass fibers. According to a certain aspect, the one or more fillers includes glass fibers as a weight percent of the filler of about 25% glass fibers. According to a certain aspect, the one or more fillers includes glass particles. According to a certain aspect, the one or more fillers includes glass particles as a weight percent of the filler of about 65% to about 85% glass particles. According to a certain aspect, the one or more fillers includes glass particles as a weight percent of the filler of about 75% glass fibers. According to one aspect, the filler includes as a weight percent of the composition about 55% to about 75% silanized barium boroalumina silicate glass filler. According to one aspect, the filler includes as a weight percent of the composition about 61% to about 68% or about 66% to about 70% silanized barium boroalumina silicate glass filler. According to one aspect, the filler includes as a weight percent of the composition about 1% to about 10% silanized fumed silica filler. According to one aspect, the filler includes as a weight percent of the composition about 3% to about 8% silanized fumed silica filler.

According to one aspect, the compositions of the present disclosure include an effective sterilizing amount of a sterilizing agent. According to one aspect, the compositions of the present disclosure include as a weight percent of the composition about 1.0% to about 4.0% of a sterilizing agent. According to one aspect, the compositions of the present disclosure include as a weight percent of the composition about 2.0% to about 2.5% of a sterilizing agent. According to one aspect, the sterilizing agent is glutaraldehyde which may be referred to as glutar(di)aldehyde.

According to one aspect, the compositions of the present disclosure include a calcium phosphate precipitating compound. According to one aspect, the compositions of the present disclosure include as a weight percent of the composition about 2% to about 7% of the calcium phosphate precipitating compound. According to one aspect, the compositions of the present disclosure include as a weight percent of the composition about 3.0% to about 5.0% of a calcium phosphate precipitating compound. According to one aspect, the calcium phosphate precipitating compound is hydroxyapatite.

According to one aspect, one of skill in the art will recognized based on the present disclosure that the percent ranges of ingredients may apply to a total blended composition or to individual formulations that are to be blended together to form a total blended composition. For example, individual formulations, such as two separate formulations having specific ingredients may be made into two separate viscous mixtures, and then the two separate formulations may be blended together, such as with a dual chamber syringe having a static mixer. Each separate formulation is placed into a chamber. A plunger causes each of the separate formulations to exit their respective chamber and to enter a static mixer where the two separate formulations are mixed.

One of ordinary skill in the art will recognize based on the present disclosure that various ingredients used to make dental composites or bone composites and the like described herein can be combined with the antipathogenic agents or sterilizing agents of the present disclosure to render the dental composites or bone composites antipathogenic or sterile. Such composites or compositions can be one component formulations. Such composites or compositions can be two component formulations that are mixed prior to use. One of ordinary skill in the art will appreciate based on the present disclosure that the percentages described herein are exemplary only and that percentages can be altered depending on the desired ingredients and whether the dental composite bone cement and the like is a one component, two component or multicomponent formulation.

According to one aspect, the compositions described herein are created by mixing together ingredients using methods known to those of skill in the art. According to one aspect, the ingredients of a component are blended together without the antipathogenic agent or sterilizing agent and the antipathogenic agent or sterilizing agent is mixed into the blend as a final ingredient. The ingredients of one component formulations or the ingredients of separate components of two component formulations, for example, are blended together using mixing devices known to those of skill in the art for blending together ingredients. In addition, companies are known to those of skill in the art which blend ingredients into formulations based on an ingredient list.

An exemplary two component formulation, i.e. Part A and Part B, is presented in the Table 1 below.

| SPECIFICATION FOR PART A | |
| --- | --- |
| Bis-phenol A glycidyl dimethacrylate (BisGMA):Ethoxylated Bis-phenol A dimethacrylate (BisEMA), 1:1 | 11-23 wt-% |
| Triethylene glycol dimethacrylate (TEGDMA) | 7-13 wt-% |
| Barium boroalumina silicate glass filler, maximum particle size 20 micrometer, silanized | 61-68 wt-% |
| Fumed silica filler, maximum particle size 5 micron, silanized | 3-8 wt % of silicate glass filler |
| Glutar(di)aldehyde (GA) | 2-2.5% |
| Dimethyl-p-toluidine (DMPT) | 2-5 wt-% |
| Hydroxyapatite powder (HA), maximum particle size 20 micrometer | 3-5 wt-% |
| Butylated hydroxytoluene (BHT) | 0.2-0.5 wt-% |
| SPECIFICATION FOR PART B | |
| Bis-phenol A glycidyl dimethacrylate (BisGMA):Ethoxylated Bis-phenol A dimethacrylate (BisEMA), 1:1 | 11-23 wt-% |
| Triethylene glycol dimethacrylate (TEGDMA) | 7-13 wt-% |
| Barium boroalumina silicate glass filler, maximum particle size 20 micrometer, silanized | 66-70 wt-% |
| Fumed silica filler, maximum particle size 5 micrometer, silanized | 3-8 wt % of silicate glass filler |
| Glutar(di)aldehyde (GA) | 2-2.5% |
| Benzoyl peroxide (BPO) | 1-4 wt-% |
| Butylated hydroxytoluene (BHT) | 0.2-0.5 wt-% |

It is to be understood that microbes and/or bacteria and/or fungus and/or yeast are singly or collectively referred to herein as a pathogen or pathogens. Since the amount of live or viable microbes and/or bacteria and/or fungus and/or yeast within compositions described herein is reduced or eliminated, such as with a sterile condition, the risk of microbial and/or bacterial and/or fungal and/or yeast infection or illness to an individual within which the composition is placed is also reduced according to certain embodiments of the present invention. It is to be understood that one of skill in the art will readily envision species of pathogens such as microbes, bacteria, fungi and yeast based on the present disclosure using standard references. Bacteria within the scope of the present disclosure include *Staphylococcus aureus, B. Atrophaeus, S. Albicans, A. Niger, Staphylococcus epidermidis, Pseudomonas aeruginosa,* MRSA, *E. coli,* candida (yeast), *Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium tuberculosis, Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium,* Enterobacteriaceae, *Staphylococcus saprophyticus* and the like. The above list is intended to be exemplary and not exhaustive. One of skill in the art will readily be able to identify additional bacteria within the scope of the present disclosure. Yeast within the scope of the present disclosure include *Cryptococcus neoformans, S. cerevisiae, Rhodotorula rubra, Torulopsis* and *Trichosporon cutaneum, Schizosaccharomyces pombe, Saccharomyces pastorianus, S. carlsbergensis, S. boulardii* and *C. albicans*. The above list is intended to be exemplary and not exhaustive. One of skill in the art will readily be able to identify additional yeast within the scope of the present disclosure.

Methods according to the present disclosure to make the compositions described herein include mixing or otherwise combining ingredients into a homogenous or substantially homogenous composition. Mixing can be accomplished by using commercially available mixing or blending devices such as Speedmixer available from Hauschild Engineering. Mixing can also be accomplished by hand using a suitable spatula or other mixing device. Dry and liquid components can be combined into a single vessel and the components blended into a homogeneous composition. Dry ingredients can be mixed together and then the dry ingredient mixture can be added to a liquid component for blending. Dry ingredients can be added to the liquid component in a vessel one at a time or together as a dry mixture. The components are then blended into a homogeneous composition. Dry ingredients can be added to a vessel and then a liquid component can be added to a vessel. The components are then blended into a homogeneous composition. Ingredients can be added in any order for blending and the blending can be carried out while ingredients are added to the vessel. It is to be understood that the blending of certain ingredients in a particular order or amount may be preferred in facilitating production of a final blended composition. One of ordinary skill in the art based on the present disclosure can combine various dry and liquid ingredients in various orders or amounts and for various blending time periods to create homogeneous or substantially homogeneous compositions including sterilizing agents in an amount effective to render the composition sterile.

The ability of the compositions of the present invention to remain sterile is determined by methods known to those of skill in the art including the protocol described in ISO 11737-2 hereby incorporated by reference in its entirety.

EXAMPLE I

Three batches each of a two component formulation of composite A and composite B described in Table 1, each with 2% glutaraldehyde were tested for antipathogenic effect on each of *Pseudomonas aeruginosa, Staphylococcus aureus* and *Aspergillus brasiliensis* as follows.

Mixing and inoculation of the composites for the investigation: 4800 mg of each composite was weighed in a separate beaker glass with a magnetic stir bar inside. The beaker glass was covered with a peace of aluminium foil. Then, 200 µl of the glutaraldehyde (50% aqueous solution) was added and mixed on a magnetic stirrer for 5 minutes at 150 rpm. After this time, 100 µl of the suspension of the microorganisms were added and mixing was continued for 5 minutes at 200 rpm. The calculated colony count in each beaker glass was >$10^6$ cfu. The controls consisted of 5000 mg of composite mixed with 100µ l of the suspension of the microorganisms with the magnetic stirrer for 5 minutes at 200 rpm. The glass beakers with the samples were stored at room temperature.

Determination of the colony counts of the microorganisms: For the determination of the colony counts of the microorganisms a sample of the mixture of 500 mg was taken out of the beaker glass with a sterile cotton swab. The cotton swab was then transferred into a test tube filled with 10 ml TLH-Thio solution. The cotton swab remained in the test tube. The test tube was placed in an activated ultrasonic bath at room temperature for 15 minutes and was afterwards shaken with the vortex. To investigate the samples with glutaraldehyde, 1 ml and 0.1 ml of each TLH-Thio-eluate were plated on TSA plates in the case of the microorganisms *Staphylococcus aureus* and *Pseusdomonas aeruginosa* and on MEA plates in the case of *Aspergillus brasiliensis*. The TSA plates were incubated for 24 h at 36±2° C. and the MEA plates were incubated for 7 days at 30±2° C. before the colony counts were determined. For the examination of the controls, a serial dilution from each TLH-Thio-eluate was made with dilution solution in equal step sizes with a dilution-fold of 1:10. Then, 1 ml of the TLH-Thio-eluate and also 1 ml of each dilution up to $10^{-4}$ were plated on TSA plates in the case of *Staphylococcus aureus* and *Pseusdomonas aeruginosa* and on MEA plates in the case of *Aspergillus brasiliensis*. The TSA plates were incubated for 24 h at 36±2° C. and the MEA plates were incubated for 7 days at 30±2° C. before the colony counts were determined. Table 2 below shows the results of the colony counts of the controls with *Staphylococcus aureus*. The used suspension had a concentration of 7.5×$10^8$ cfu/ml, which corresponded to 7.5×$10^7$ cfu per beaker glass.

TABLE 2

Results of colony counts of the controls with *Staphylococcus aureus*.

| Composite | Sample | Dilution | cfu on plate | Cfu/beaker glass[1] |
|---|---|---|---|---|
| A | 1 | 0 | 193 | 1.9 × $10^4$ |
|  |  | $10^{-1}$ | 20 |  |
|  |  | $10^{-2}$ | 2 |  |
|  |  | $10^{-3}$ | 0 |  |
|  |  | $10^{-4}$ | 0 |  |
|  | 2 | 0 | 118 | 1.3 × $10^4$ |
|  |  | $10^{-1}$ | 22 |  |
|  |  | $10^{-2}$ | 0 |  |
|  |  | $10^{-3}$ | 0 |  |
|  |  | $10^{-4}$ | 0 |  |
|  | 3 | 0 | 128 | 1.3 × $10^4$ |
|  |  | $10^{-1}$ | 14 |  |
|  |  | $10^{-2}$ | 1 |  |
|  |  | $10^{-3}$ | 0 |  |
|  |  | $10^{-4}$ | 0 |  |
| B | 1 | 0 | 0 | 0 |
|  |  | $10^{-1}$ | 0 |  |

TABLE 2-continued

Results of colony counts of the controls with *Staphylococcus aureus*.

| Composite | Sample | Dilution | cfu on plate | Cfu/beaker glass[1] |
|---|---|---|---|---|
| | | $10^{-2}$ | 0 | |
| | | $10^{-3}$ | 0 | |
| | | $10^{-4}$ | 0 | |
| | 2 | 0 | 0 | 0 |
| | | $10^{-1}$ | 0 | |
| | | $10^{-2}$ | 0 | |
| | | $10^{-3}$ | 0 | |
| | | $10^{-4}$ | 0 | |
| | 3 | 0 | 0 | 0 |
| | | $10^{-1}$ | 0 | |
| | | $10^{-2}$ | 0 | |
| | | $10^{-3}$ | 0 | |
| | | $10^{-4}$ | 0 | |

[1]Weighted average of the colony counts

Table 3 below shows the results for Batch 1.

TABLE 3

Table 3: Results of colony counts of batch 1 with *Staphylococcus aureus*.
Batch 1

| Composite | Sample | Dilution | cfu on plate | Cfu/beaker glass[1] |
|---|---|---|---|---|
| A | 1 | 0 | 0 | 0 |
| | | $10^{-1}$ | 0 | |
| | 2 | 0 | 0 | 0 |
| | | $10^{-1}$ | 0 | |
| | 3 | 0 | 0 | 0 |
| | | $10^{-1}$ | 0 | |
| B | 1 | 0 | 0 | 0 |
| | | $10^{-1}$ | 0 | |
| | 2 | 0 | 0 | 0 |
| | | $10^{-1}$ | 0 | |
| | 3 | 0 | 0 | 0 |
| | | $10^{-1}$ | 0 | |

[1]Weighted average of the colony counts

Table 4 below shows the results for Batch 2.

TABLE 4

Table 4: Results of colony counts of batch 2 with *Staphylococcus aureus*.
Batch 2

| Composite | Sample | Dilution | cfu on plate | Cfu/beaker glass[1] |
|---|---|---|---|---|
| A | 1 | 0 | 0 | 0 |
| | | $10^{-1}$ | 0 | |
| | 2 | 0 | 0 | 0 |
| | | $10^{-1}$ | 0 | |
| | 3 | 0 | 0 | 0 |
| | | $10^{-1}$ | 0 | |
| B | 1 | 0 | 0 | 0 |
| | | $10^{-1}$ | 0 | |
| | 2 | 0 | 0 | 0 |
| | | $10^{-1}$ | 0 | |
| | 3 | 0 | 0 | 0 |
| | | $10^{-1}$ | 0 | |

[1]Weighted average of the colony counts

Table 5 below shows the results for Batch 3.

TABLE 5

Table 5: Results of colony counts with batch 3.
Batch 3

| Composite | Sample | Dilution | cfu on plate | Cfu/beaker glass[1] |
|---|---|---|---|---|
| A | 1 | 0 | 0 | 0 |
| | | $10^{-1}$ | 0 | |
| | 2 | 0 | 0 | 0 |
| | | $10^{-1}$ | 0 | |
| | 3 | 0 | 0 | 0 |
| | | $10^{-1}$ | 0 | |
| B | 1 | 0 | 0 | 0 |
| | | $10^{-1}$ | 0 | |
| | 2 | 0 | 0 | 0 |
| | | $10^{-1}$ | 0 | |
| | 3 | 0 | 0 | 0 |
| | | $10^{-1}$ | 0 | |

[1]Weighted average of the colony counts

Table 6 below shows the results of the colony counts of the controls with *Pseusdomonas aeruginosa*. The used suspension had a concentration of $4.3 \times 10^9$ cfu/ml, which corresponded to $4.4 \times 10^8$ cfu per beaker glass.

TABLE 6

Table 6: Results of colony counts of the controls with *Pseudomonas aeruginosa*.

| Composite | Sample | Dilution | cfu on plate | Cfu/beaker glass[1] |
|---|---|---|---|---|
| A | 1 | 0 | 0 | 0 |
| | | $10^{-1}$ | 0 | |
| | | $10^{-2}$ | 0 | |
| | | $10^{-3}$ | 0 | |
| | | $10^{-4}$ | 0 | |
| | 2 | 0 | 0 | 0 |
| | | $10^{-1}$ | 0 | |
| | | $10^{-2}$ | 0 | |
| | | $10^{-3}$ | 0 | |
| | | $10^{-4}$ | 0 | |
| | 3 | 0 | 0 | 0 |
| | | $10^{-1}$ | 0 | |
| | | $10^{-2}$ | 0 | |
| | | $10^{-3}$ | 0 | |
| | | $10^{-4}$ | 0 | |
| B | 1 | 0 | 0 | 0 |
| | | $10^{-1}$ | 0 | |
| | | $10^{-2}$ | 0 | |
| | | $10^{-3}$ | 0 | |
| | | $10^{-4}$ | 0 | |
| | 2 | 0 | 0 | 0 |
| | | $10^{-1}$ | 0 | |
| | | $10^{-2}$ | 0 | |
| | | $10^{-3}$ | 0 | |
| | | $10^{-4}$ | 0 | |
| | 3 | 0 | 0 | 0 |
| | | $10^{-1}$ | 0 | |
| | | $10^{-2}$ | 0 | |
| | | $10^{-3}$ | 0 | |
| | | $10^{-3}$ | 0 | |

[1]Weighted average of the colony counts

Table 7 shows the results for Batch 1.

TABLE 7

Table 7: Results of colony counts of batch 1 with *Pseudomonas aeruginosa*.
Batch 1

| Composite | Sample | Dilution | cfu on plate | Cfu/beaker glass[1] |
|---|---|---|---|---|
| A | 1 | 0 | 0 | 0 |
|   |   | $10^{-1}$ | 0 |   |
|   | 2 | 0 | 0 | 0 |
|   |   | $0^{-1}$ | 0 |   |
|   | 3 | 0 | 0 | 0 |
|   |   | $10^{-1}$ | 0 |   |
| B | 1 | 0 | 0 | 0 |
|   |   | $0^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |

[1] Weighted average of the colony counts

Table 8 shows the results for Batch 2.

TABLE 8

Table 8: Results of colony counts of batch 2 with *Pseudomonas aeruginosa*.
Batch 2

| Composite | Sample | Dilution | cfu on plate | Cfu/beaker glass[1] |
|---|---|---|---|---|
| A | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |
| B | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |

[1] Weighted average of the colony counts

Table 9 shows the results for Batch 3.

TABLE 9

Table 9: Results of colony counts of batch 3 with *Pseudomonas aeruginosa*.
Batch 3

| Composite | Sample | Dilution | cfu on plate | Cfu/beaker glass[1] |
|---|---|---|---|---|
| A | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |
| B | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |

[1] Weighted average of the colony counts

Table 10 below shows the results of the colony counts of the controls with *Aspergillus brasiliensis*. The used suspension had a concentration of $6.7 \times 10^7$ cfu/ml, which corresponded to $6.7 \times 10^8$ cfu per beaker glass.

TABLE 10

Table 10: Results of colony counts of the controls with *Aspergillus brasiliensis*.

| Composite | Sample | Dilution | cfu on plate | Cfu/beaker glass[1] |
|---|---|---|---|---|
| A | 1 | 0 | >300 | $8.1 \times 10^4$ |
|   |   | $10^{-1}$ | 75 |   |
|   |   | $10^{-2}$ | 14 |   |
|   |   | $10^{-3}$ | 0 |   |
|   |   | $10^{-4}$ | 0 |   |
|   | 2 | 0 | 150 | $1.7 \times 10^4$ |
|   |   | $10^{-1}$ | 29 |   |
|   |   | $10^{-2}$ | 8 |   |
|   |   | $10^{-3}$ | 1 |   |
|   |   | $10^{-4}$ | 0 |   |
|   | 3 | 0 | >300 | $5.2 \times 10^4$ |
|   |   | $10^{-1}$ | 50 |   |
|   |   | $10^{-2}$ | 6 |   |
|   |   | $10^{-3}$ | 2 |   |
|   |   | $10^{-4}$ | 0 |   |
| B | 1 | 0 | 24 | $2.4 \times 10^4$ |
|   |   | $10^{-1}$ | 2 |   |
|   |   | $10^{-2}$ | 0 |   |
|   |   | $10^{-3}$ | 0 |   |
|   |   | $10^{-4}$ | 0 |   |
|   | 2 | 0 | 17 | $1.6 \times 10^3$ |
|   |   | $10^{-1}$ | 1 |   |
|   |   | $10^{-2}$ | 0 |   |
|   |   | $10^{-3}$ | 0 |   |
|   |   | $10^{-4}$ | 0 |   |
|   | 3 | 0 | 8 | $8.0 \times 10^2$ |
|   |   | $10^{-1}$ | 0 |   |
|   |   | $10^{-2}$ | 0 |   |
|   |   | $10^{-3}$ | 0 |   |
|   |   | $10^{-4}$ | 0 |   |

[1] Weighed average of the colony counts

Table 11 shows the results for Batch 1.

TABLE 11

Table 11: Results of colony counts of batch 1 with *Aspergillus brasiliensis*.
Batch 1

| Composite | Sample | Dilution | cfu on plate | Cfu/beaker glass[1] |
|---|---|---|---|---|
| A | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |
| B | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |

[1] Weighted average of the colony counts

Table 12 shows the results for Batch 2.

TABLE 12

Table 12: Results of colony counts of batch 2 with *Aspergillus brasiliensis*.
Batch 2

| Composite | Sample | Dilution | cfu on plate | Cfu/beaker glass[1] |
|---|---|---|---|---|
| A | 1 | 0 | 0 | 0 |
|   |   | $0^{-1}$ | 0 |   |
|   | 1 | 0 | 0 | 0 |
|   |   | $10^{-1}$ | 0 |   |
|   | 3 | 0 | 0 | 0 |
|   |   | $10^{-1}$ | 0 |   |

TABLE 12-continued

Table 12: Results of colony counts of
batch 2 with *Aspergillus brasiliensis*.
Batch 2

| Composite | Sample | Dilution | cfu on plate | Cfu/beaker glass[1] |
|---|---|---|---|---|
| B | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |

[1]Weighted average of the colony counts

Table 13 shows the results of Batch 3.

TABLE 13

Table 13: Results of colony counts of
batch 3 with *Aspergillus brasiliensis*.
Batch 3

| Composite | Sample | Dilution | cfu of plate | Cfu/beaker glass[1] |
|---|---|---|---|---|
| A | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |
| B | 1 | 0 | 0 | 0 |
|   |   | $10^{-1}$ | 0 |   |
|   | 2 | 0 | 0 | 0 |
|   |   | $10^{-1}$ | 0 |   |
|   | 3 | 0 | 0 | 0 |
|   |   | $10^{-1}$ | 0 |   |

[1]Weighted average of the colony counts

EXAMPLE II

The following properties of a bone cement formulation described in Table 1 with and without glutaraldehyde (GA) were determined as follows.

Bending strength: A set amount of the dual paste system was injected into a mount to form a set cement shape of width 2 mm and height 2 mm. The cement was allowed to set and was then carefully removed. The width and height of each specimen was separately measured before placing each specimen to be tested on the material testing machine. The test protocol followed the guidelines of ISO 4049: 2009. The maximum load at which the specimen failed under four point bending load was determined. For the bone cement having 0% GA, the average bending strength was 97 MPa with a standard deviation of 12 MPa. For the bone cement having 1% GA, the average bending strength was 95 MPa with a standard deviation of 11 MPa.

Compressive strength: A set amount of the dual paste system was injected into a mount to form a set cement shape of diameter 4 mm and length 6 mm. The cement was allowed to set and was then carefully removed. The diameter and length of each specimen was separately measured before placing each specimen to be tested on the material testing machine. The test protocol followed the guidelines of ISO 9917-1:2007. The maximum load at which the specimen failed under compressive load was determined. For the bone cement having 0% GA, the average compressive strength was 202 MPa with a standard deviation of 7 MPa. For the bone cement having 1% GA, the average compressive strength was 211 MPa with a standard deviation of 14 MPa.

Setting: All tests were carried out at room temperature. The working time, setting time and maximum setting temperature were measured according to ISO 5833: 2002 Annex C, except that the injected volume was 1 ml. The temperature was measured using a K-type thermocouple and a data-logger. A 5 ml disposable syringe was utilized as mould and the thermocouple was inserted thru the nozzle and it extended 3 mm into the chamber. Two determinations were conducted as specified in Annex C of ISO5833: 2002. For the bone cement having 0% GA, the maximum setting temperature was 48° C., the setting time (as specified in ISO5833) was 06:00 (min:sec); For the bone cement having 1% GA, the maximum setting temperature was 46° C., the setting time (as specified in ISO5833) was 05:45 (min:sec); For the bone cement having 2.5% GA, the maximum setting temperature was 48° C., the setting time (as specified in ISO5833) was 05:45 (min:sec).

The invention claimed is:

1. A syringe having a first compartment, a second compartment, a plunger and a static mixer whereby depressing the plunger forces ingredients from the first compartment and the second compartment through the static mixer and outside of the syringe
wherein the first compartment includes one or more polymerizable compounds, one or more glass filler compounds, one or more sterilizing agents, one or more polymerization accelerators, one or more calcium phosphate precipitating compounds and one or more free-radical scavenger compounds; and
wherein the second compartment includes one or more polymerizable compounds, one or more glass filler compounds, one or more sterilizing agents, one or more polymerization initiators, one or more calcium phosphate precipitating compounds and one or more free-radical scavenger compounds, wherein the one or more sterilizing agents is glutaraldehyde present in an amount between about 2.0 wt % and about 2.5 wt %.

2. The syringe of claim 1 wherein the one or more polymerizable compounds includes an acrylate compound.

3. The syringe of claim 2 wherein the acrylate compound includes one or more of bis-phenol A glycidyl dimetharcylate, ethoxylated bis-phenol A dimethacrylate or triethylene glycol dimethacrylate.

4. The syringe of claim 1 wherein the one or more glass filler compounds includes one or more of barium boroalumina silicate or fumed silica.

5. The syringe of claim 1 wherein the one or more sterilizing agents further includes one or more of organic acids, benzoic acid, scorbic acid, organic esters, parabens, methyl, ethyl, propyl and butyl esters of para-(4)-hydroxy benzoic acid, quaternary ammonium compounds, biguanides, chlorhexidine, chlorhexidine diacetate, chlorhexidine gluconate, organomercurial compounds, phenylmercuric nitrate, phenyl mercuric acetate, phenyl mercuric acid, merthiolate, alcohols, ethanol, methanol, propan-1-ol, propan-2-ol, phenyl ethanol, aldehyde compounds, formaldehyde, glyoxal, malonaldehyde, succinaldehyde, adipaldehyde, halogen compounds, iodine, iodine compounds, iodophors, chlorine, chlorine compounds, chlorine releasing compounds, calcium hypochlorite, sodium dichloroisocyanusate, hypochlorous acid, mercuric chloride, benzalkonium chloride, cetylpyridinium chloride, hydrogen peroxide, peroxy acids, peracetic acid, peroxygens, propiolactone, β-propiolactone, peracetic acid, cupric ascrobate, sodium hypochlorite, sodium thioglycolate, phenol, cresol, or chlorocresol.

6. The syringe of claim 1 wherein the one or more polymerization initiators includes benzoyl peroxide.

7. The syringe of claim 1 wherein the one or more polymerization accelerators includes dimethyl-p-toluidine.

8. The syringe of claim 1 wherein the one or more free-radical scavenger compounds includes butylated hydroxytoluene.

9. The syringe of claim 1 wherein the one or more sterilizing agents is stable without the use of a separate stabilizing compound.

10. The syringe of claim 1 wherein the one or more sterilizing agents consists essentially of glutaraldehyde.

11. The syringe of claim 1 wherein the calcium phosphate precipitating compound is hydroxyapatite.

* * * * *